June 15, 1976
J. C. MIKKELSEN
BEGONIA PLANT
Filed May 5, 1975
Plant Pat. 3,913
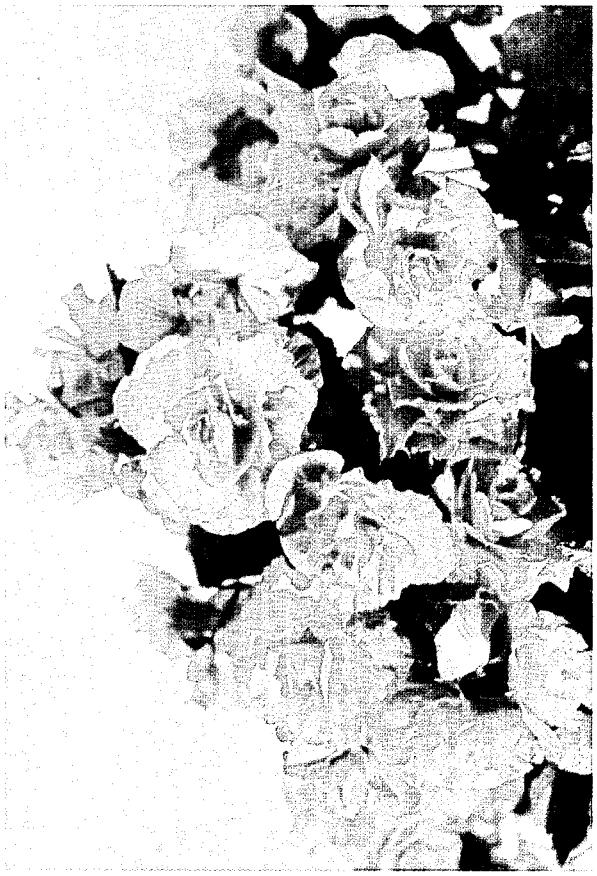

United States Patent

Plant Pat. 3,913

Patented June 15, 1976

3,913

BEGONIA PLANT

James C. Mikkelsen, Ashtabula, Ohio, assignor to Mikkelsens Inc., Ashtabula, Ohio Filed May 5, 1975, Ser. No. 574,626

Int. Cl. A01h *5/00*

U.S. Cl. Plt.—68 1 Claim

The present invention relates to a new and distinctive variety of begonia plant known by the cultivar name Red Elegance and botanically known as *Begonia elatior*. The new cultivar was discovered by me as a spontaneous sibling mutation (one of three) from a very bright deep rose red double flowering begonia identified by code number 8252 that was never commercialized. The parent cultivar was a previous mutation from Aphrodite Rose, an unpatented commercial cultivar. Asexual reproduction by stem and leaf cuttings has reproduced the unique features of the new cultivar through successive propagations.

The following characteristics distinguish the new begonia from both its parent and other begonias commercially known and used in the floriculture industry:

(1) Compared to the deep rose red flowers of the parent variety the flower color of Red Elegance is a clearer red. The red flower color is more distinct than in Aphrodite Red, an unpatented commercial cultivar.

(2) The flower size is somewhat larger than the parent variety which measures 7–8 cm. as compared with Red Elegance which measures 8–9 cm. in diameter.

(3) The edges of the tepals are serrated and ruffled and the center tepals are swirled, giving the flower a definite appearance of a camellia.

(4) A unique characteristic of the individual flowers is "flower-in-flower" effect giving added depth to individual flowers as in azaleas. The tepals may separate into three or four groups during the life of the bloom.

(5) When Red Elegance is compared to Elegance, another mutation of #8252 disclosed and claimed in my pending application Ser. No. 574,628, filed May 5, 1975 the two cultivars are similar except for flower color and size. The flower size of Elegance is slightly greater and the tepal color is a light shade of pink.

(6) Compared to Rieger Aphrodite begonia types that are propagated mostly by vegetative top or stem cuttings, Red Elegance propagates by leaf cuttings that develop multiple adventitious shoots. This method of propagation by leaf cuttings assures the grower of a vegetative plant for production of sizeable flowering plants.

(7) Quantity of flowers is comparable to Aphrodite Rose. However, size and depth of flowers on Red Elegance are much greater than Aphrodite Rose.

(8) The foliage is immune to powdery mildew. Foliage has superior quality and is darker green than Aphrodite Rose.

(9) The overall vigor of Red Elegance is more pronounced than in Rieger Aphrodite cultivars.

The accompanying colored photograph illustrates the overall appearance of this variety taken as a face view of the plant and showing the colors as true as it is reasonably possible to obtain in a colored reproduction of this type.

The following is a detailed description of my new begonia variety based on plants produced under commercial practices in Ashtabula, Ohio. Color references are made to the Royal Horticultural Society Colour Chart except where general color terms of ordinary dictionary significance are used.

Parentage: A spontaneous sibling mutation (one of three) that was found in begonia plant #8252 which was a mutation selected out of Aphrodite Rose.

Propagation: By vegetative top or stem cuttings that will root in 28 to 30 days. The most effective method to control flowering response is propagation by leaf cuttings that root in 30 to 35 days and eventually develop vegetative adventitious shoots from the base of the leaf petiole.

Rooting habit: Is considered near average for this type begonia with fine, numerous, dendritic roots.

Plant form: Tends to be more upright than procumbent, Where properly supported, this new cultivar develops into a pleasing upright standard type begonia plant. Young, soft growth can be trained for baskets.

Habit of growth: Vigorous, fast growing, self-branching.

Blooming habits: Is free flowering in all seasons. Flowering is slightly inhibited under high light intensity, more than 12 hours daylength, and temperatures constantly above 75° day and night.

Blooming season: Indeterminant by season. Best manipulated by using vegetative plants from leaf cuttings as it is often difficult to obtain vegetative stem cuttings.

Foliage: Average quantity for this type of elatior begonia.

Size: Considered moderately large measuring 10 cm. wide by 12 cm. long when plants are grown under commercial practices in Ashtabula, Ohio.

Shape: Cordate.

Texture: Smooth, waxy, thick extreme protrusion of veins on underside of leaf.

Margin: some serration, twisting in sinus areas.

Color: Young—upperside, green 137A–B, underside, green 147C, very fine serration on edges in young leaves. Mature—upperside green between 137A and 147A underside green 147C with some dull red infusion.

Disease resistance: Apparently immune to powdery mildew when grown in areas of mildew infected plants. Only very slightly susceptible to *Xanthomonas begoniae*.

FLOWERS

Borne: On compound cyme—flowers continuously over a long period of time. Plants have been observed to be in flowering state for 12 months.

Quantity: Average for this type of begonia.

Buds: Flat—approximately 10–12 mm. in diameter before opening. Reverse of tepal before opening is light red.

Tepals: Edges are serrated and ruffled, center tepals have a swirl, color red between 42A and 44A fading to 42C.

Reproductive organs: None found to date.

I claim:

1. A new and distinct cultivar of begonia plant characterized particularly by the combined characteristics of red tepal color and unique "flower-in-flower" form which gives added depth to individual flowers; propagatable by leaf cuttings that develop vegetative adventitious shoots, superior foliage quality, with the foliage being immune to powdery mildew, and by its vigorous and upright growth habit.

No references cited.

ROBERT E. BAGWILL, Primary Examiner